United States Patent [19]

Schmieding et al.

[11] Patent Number: 5,407,069
[45] Date of Patent: Apr. 18, 1995

[54] SHAVER BLADE STERILIZATION CASE WITH BUILT-IN COUNTER

[75] Inventors: Reinhold Schmieding; Donald K. Shuler, both of Naples, Fla.

[73] Assignee: Arthrex, Inc., Naples, Fla.

[21] Appl. No.: 186,610

[22] Filed: Jan. 26, 1994

[51] Int. Cl.⁶ .................. B65D 1/34; A45D 27/29
[52] U.S. Cl. .................. 206/354; 206/370; 206/459.1
[58] Field of Search .......... 206/459.1, 363, 369, 206/370, 228, 352, 354; 116/311, 317; 30/41.7

[56] References Cited

U.S. PATENT DOCUMENTS

| | | | |
|---|---|---|---|
| 3,394,456 | 7/1968 | Gatz | 30/90 |
| 3,476,077 | 11/1969 | Henkel | 116/317 |
| 3,618,563 | 11/1971 | Singer | 116/311 |
| 4,229,420 | 10/1980 | Smith et al. | 206/363 X |
| 4,729,472 | 3/1988 | Lubin | 206/315.9 |
| 4,732,187 | 3/1988 | Mönch | 134/135 |
| 5,174,453 | 12/1992 | Stoeffler | 206/370 X |
| 5,193,678 | 3/1993 | Janocik et al. | 206/370 X |
| 5,240,107 | 8/1993 | Casale | 206/459.1 X |
| 5,279,800 | 1/1994 | Berry, Jr. | 206/369 X |
| 5,289,919 | 3/1994 | Fischer | 206/369 X |

*Primary Examiner*—Jacob K. Ackun
*Attorney, Agent, or Firm*—Ostrolenk, Faber, Gerb & Soffen

[57] ABSTRACT

A steam-autoclavable, surgical instrument sterilization case with built-in use counters. The case includes a container with a tray having sets of standoff holders for surgical instruments, a lid for covering the container and built-in counters associated with the standoffs for recording usage of the surgical instruments.

5 Claims, 5 Drawing Sheets

SHAVER BLADE STERILIZATION CASE WITH BUILT-IN COUNTER

BACKGROUND OF THE INVENTION

1. Field of the Invention

The present invention relates to a sterilization case for surgical instruments and, more specifically, to a steam-autoclavable sterilization case for arthroscopic surgical shaver blades with built-in counters for recording and tracking the usage of the shaver blades stored therein.

2. Description of the Related Art

Surgical instruments require sterilization prior to use. Sterilization procedures are carried out in various ways, including both chemical treatment and heat sterilization, typically steam autoclaving. Surgical instruments often are placed in specialized trays for sterilization purposes. Trays are used as well to provide instrument accessibility to the surgeon in the operational theater.

Surgical instruments used for cutting and shaving must be maintained with an extremely sharp cutting edge. After each use, shaver edges loose a certain degree of sharpness. Thus, shaver instruments become unusable after a given number of operations because it is not feasible to resharpen the blades. These instruments, therefore, have limited useful lives, the duration of which must be tracked in order to avoid use of worn out blades, which can be dangerous to the patient.

Disinfection containers for use in steam autoclaving and chemical sterilization are known. Chemical sterilization containers have been developed which display and record periods of time, such as the number of days required for completion of certain steps in the chemical disinfection process. See, e.g., U.S. Pat. No. 4,732,187 to Mönche. However, such devices are not equipped to display and record the remaining useful life of the instruments they contain.

Devices also are known in the prior art which record the number of uses of a razor blade, such as a safety razor. See, for example, U.S. Pat. No. 3,476,077 to Henkel and U.S. Pat. No. 3,618,563 to Singer. These devices, designed for home use by the consumer, are incapable of withstanding the rigors of steam autoclaving, and are not designed for aseptic storage and handling of precision surgical instruments.

SUMMARY OF THE INVENTION

The present invention overcomes the above-noted deficiencies of the prior art by providing a steam-autoclavable, surgical instrument sterilization case equipped with built-in counters to record the use of contained surgical instruments and to display the remaining useful life of the instruments.

In particular, the invention is a steam-autoclavable, surgical instrument sterilization and storage case comprising a container, standoffs in the container for receiving reusable surgical instruments, a lid for the container, and at least one counter for recording the number of times the surgical instruments are used.

The standoffs are provided in paired sets with notches of various sizes for receiving arthroscopic shaver blades and shaver bur instruments of various sizes. The instruments are color-coded by size. Counters are provided in correspondence with the sets of different-sized notched standoffs, the counters also being color-coded in accordance with the size of the surgical instruments received in the notched standoffs, thereby facilitating organization of the surgical instruments in the container.

The standoffs for receiving surgical instruments and the counters are mounted on a removable tray adapted to fit within the container. The removable tray includes a mounting surface which is spaced from a base of the container, thereby providing a space for storing additional instruments. A silicon finger mat is disposed on the base of the container and serves as a cushion for the additional instruments.

Other features and advantages of the present invention will become apparent from the following description of the invention which refers to the accompanying drawings.

DETAILED DESCRIPTION OF THE PREFERRED EMBODIMENT

Figure 1:
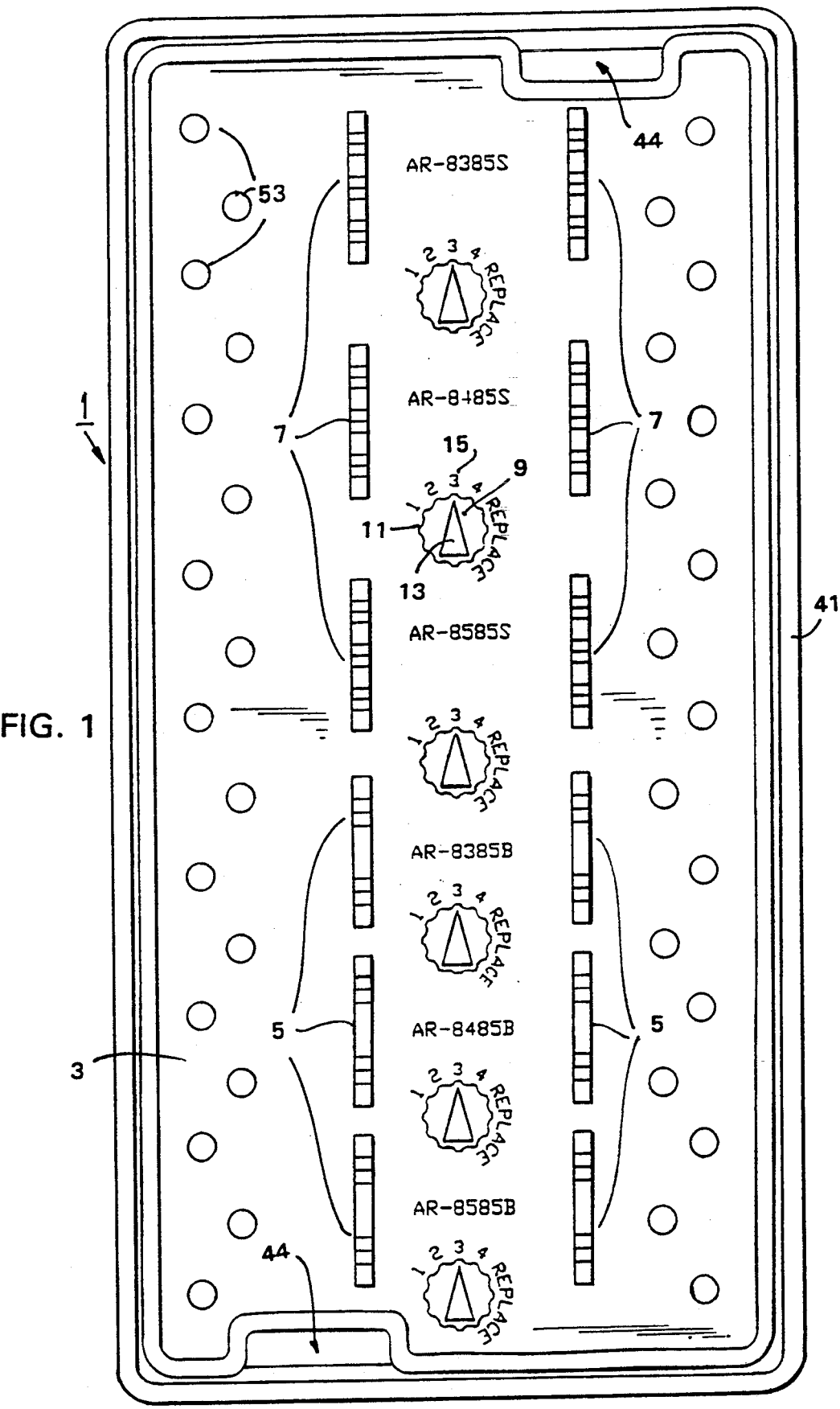
FIG. 1 shows a top view of the tray insert of the preferred embodiment.

Referring to FIG. 1, there is shown a top view of a sterilization case insert assembly 1 used in the preferred embodiment of the present invention. Insert assembly 1 has a mounting surface 3, three pairs of two-piece arthroscopic shaver bur instrument standoffs 5, three pairs of three-piece arthroscopic shaver blade standoffs 7, and a counter knob 9 associated with each pair of standoffs 5, 7. The individual standoffs of each pair are spaced apart to support surgical instruments therebetween.

As shown in FIG. 1, each counter knob 9, preferably made of polypropylene, has ridges 11 for gripping. Around the periphery of each counter knob 9 are index numbers 15 representing an instrument set's usage status. A pointer 13 on counter knob 9 is used to indicate the index number selected when the counter knob is rotated. After five uses, the index pointer registers "REPLACE," thus notifying the surgeon that the instruments should not be used again.

Figure 6:
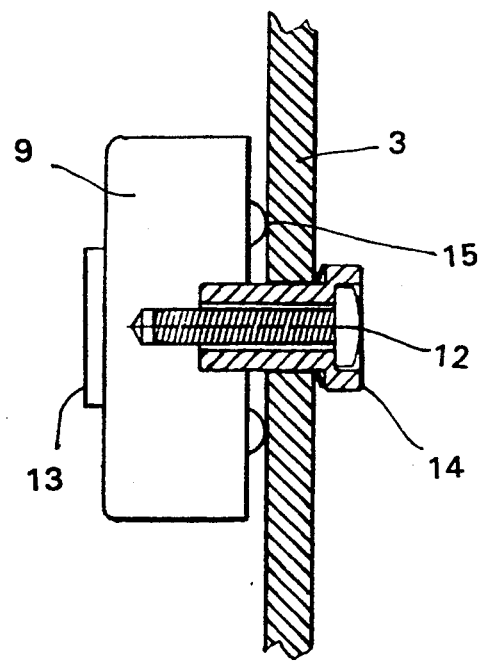
FIG. 6 is an enlarged side view of a counter assembly used in a preferred embodiment of the present invention.

Referring to FIG. 6, counter knob 9 is shown attached to mounting surface 3 via plug washer 14 and screw 12. Counter knob 9 is kept in position by bulges 15 which fit into indents (not shown) in mounting surface 3.

Figure 2:
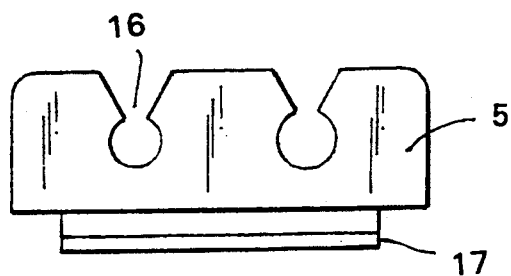
FIG. 2 is an elevation view of the standoffs for receiving a two-piece set of arthroscopic shaver bur instruments.
Figure 3:
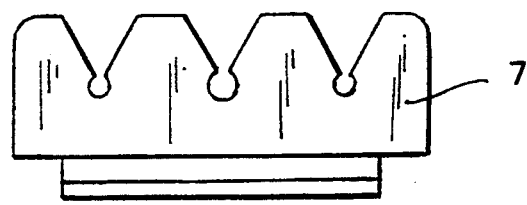
FIG. 3 is an elevation view of the standoffs for receiving a three-piece set of arthroscopic shaver blade instruments.

Standoffs 5, 7, preferably made of silicon, each have a notch 16 at their upper ends to hold surgical instruments securely for storage and to make the instruments readily available to the surgical team during operations. A tab 17 at the foot of standoffs 5, 7, fits securely into an opening (not shown) in mounting surface 3. Standoffs 5 of FIG. 2 have notches 16 which are sized to receive the two-piece shaver bur instrument set shown in FIG. 4. Similarly, standoffs 7 of FIG. 3 have notches 16 sized to hold the three-piece shaver blade instrument set of FIG. 5.

Figure 4:
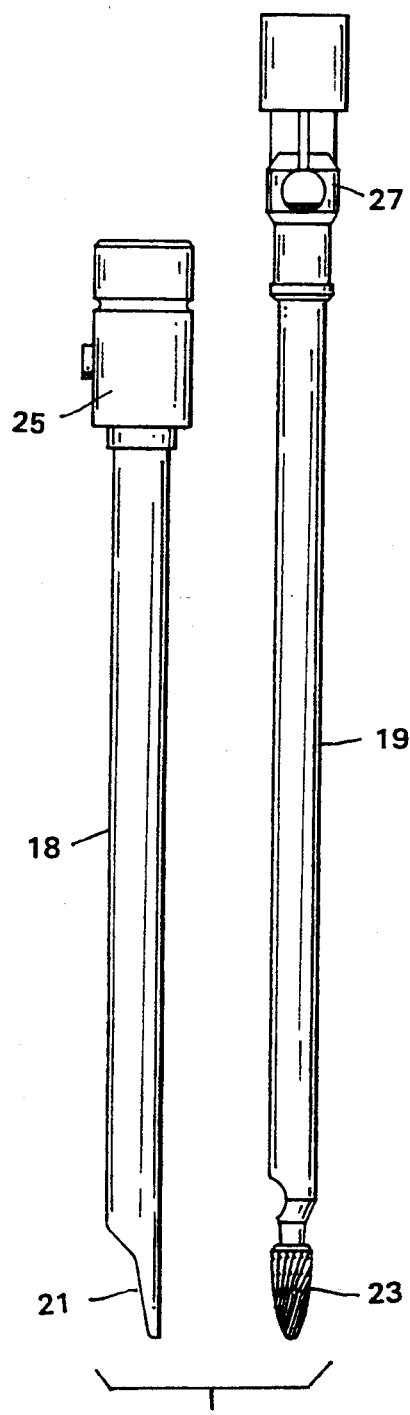
FIG. 4 is a side view of a two-piece set of arthroscopic shaver bur instruments to be received in the sterilization case.

The shaver bur set of FIG. 4 comprises an external tube 18, and an internal tube 19 inserted telescopically therein. The distal end of external tube 18 is progressively relieved to form an opening 21 for exposing a bur 23 on the distal end of internal tube 19 when the shaver tubes 18, 19 are assembled. In operation, the internal tube 19 is rotated relative to the external tube 18 by a drive train (not shown) to cause the exposed bur 23 to turn and abrade bone through opening 21. At their proximal ends, external tube 18 and internal tube 19 have hubs 25, 27, respectively, which fit within each other when the tubes are assembled. Hubs 25, 27 preferably are made of polypropylene and color-coded in correspondence with bur diameter.

Figure 5:
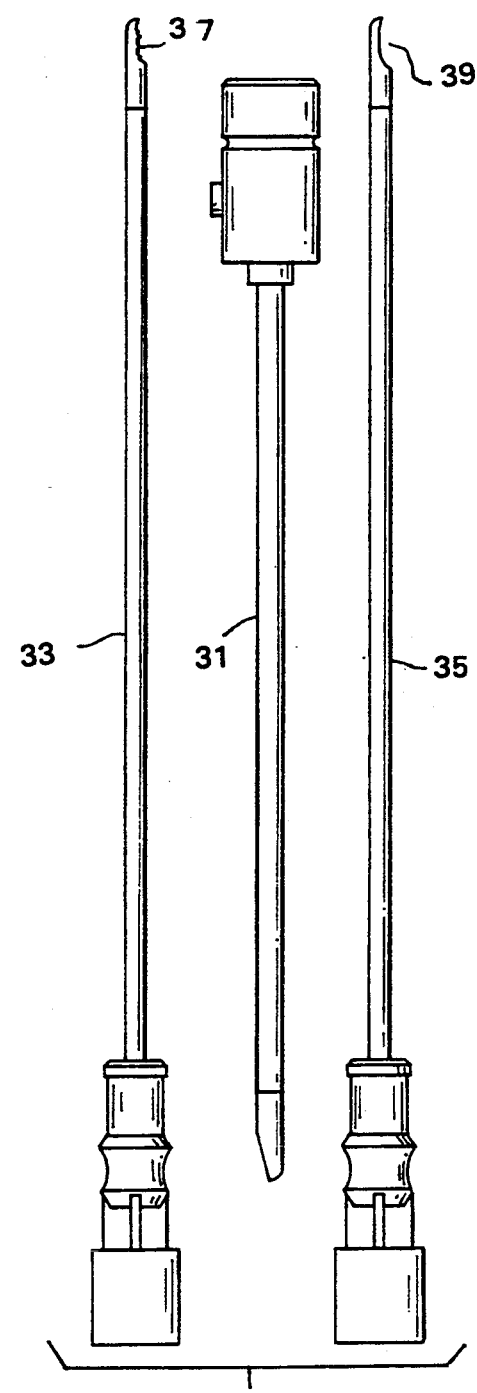
FIG. 5 is a side view of a three-piece set of arthroscopic shaver blade instruments to be received in the sterilization case.

The blade set of FIG. 5 comprises an external tube 31 which receives interchangeable internal tubes 33 and 35. Interchangeable tubes 33, 35 have shaver blades rather than burs at their distal ends. Tube 33 has a serrated blade 37, whereas tube 35 has an unserrated blade 39. Like the embodiment of FIG. 4, both external tube 31 and interchangeable internal tubes 33, 35 are provided with plastic hubs at their proximal ends. The plastic hubs are color coded in accordance with the diameter of the outer tube of the shaver blade assembly.

An assortment of three sets of shaving burs and three sets of shaving blades are held in the standoffs next to an associated counter knob. The counter knob, like the instrument hubs, is color coded in accordance with the size of the instruments held by the corresponding standoffs. Typically, the sets include a range of sizes (color coded) for each type of shaver, as follows: 3.85 (green), 4.85 (blue) and 5.85 (red) mm. diameter burs or 3.85 (green), 4.85 (blue) and 5.85 (red) mm. diameter outer tubes for blades. Thus, the same color is used for each counter and the hubs associated with each set of similarly sized instruments, which assists in organizing the instruments within the case.

Figure 7:
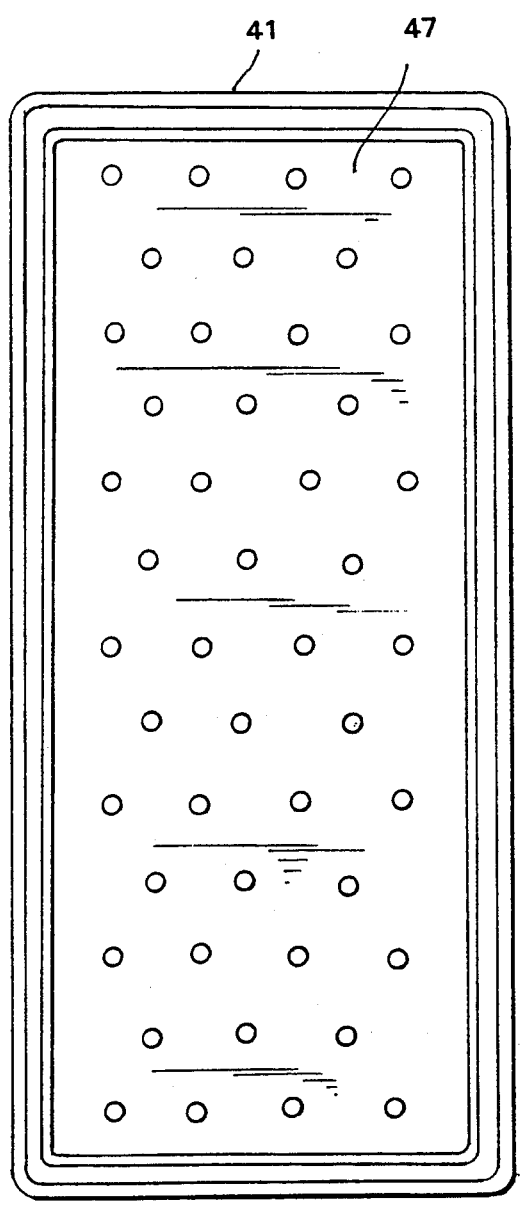
FIG. 7 is a top view of the container, finger mat and lid.
Figure 7A:
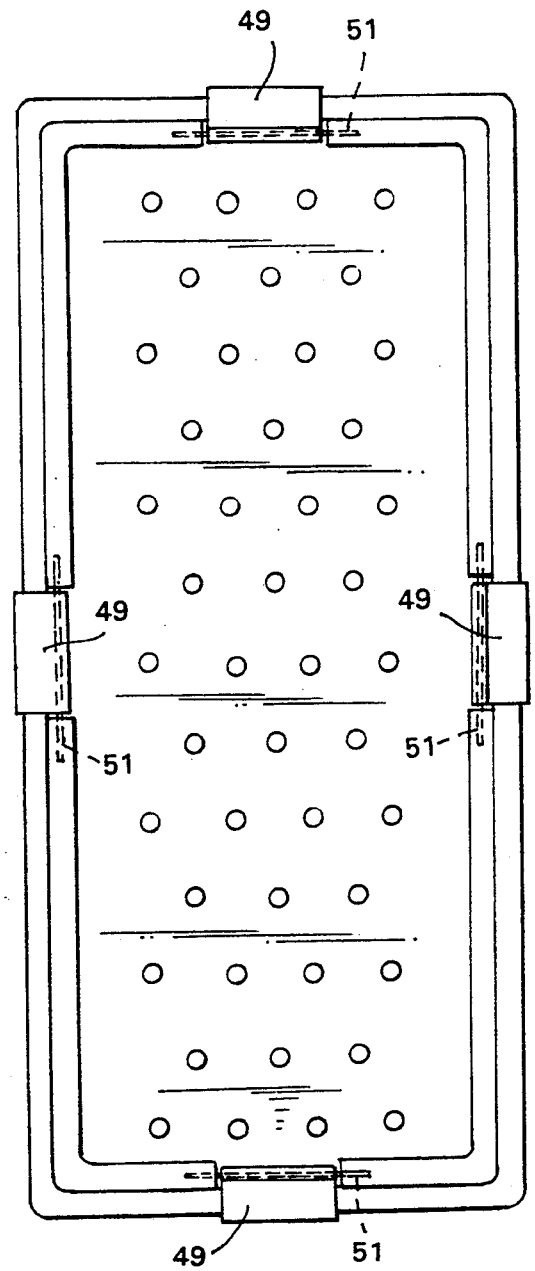
Figure 8:
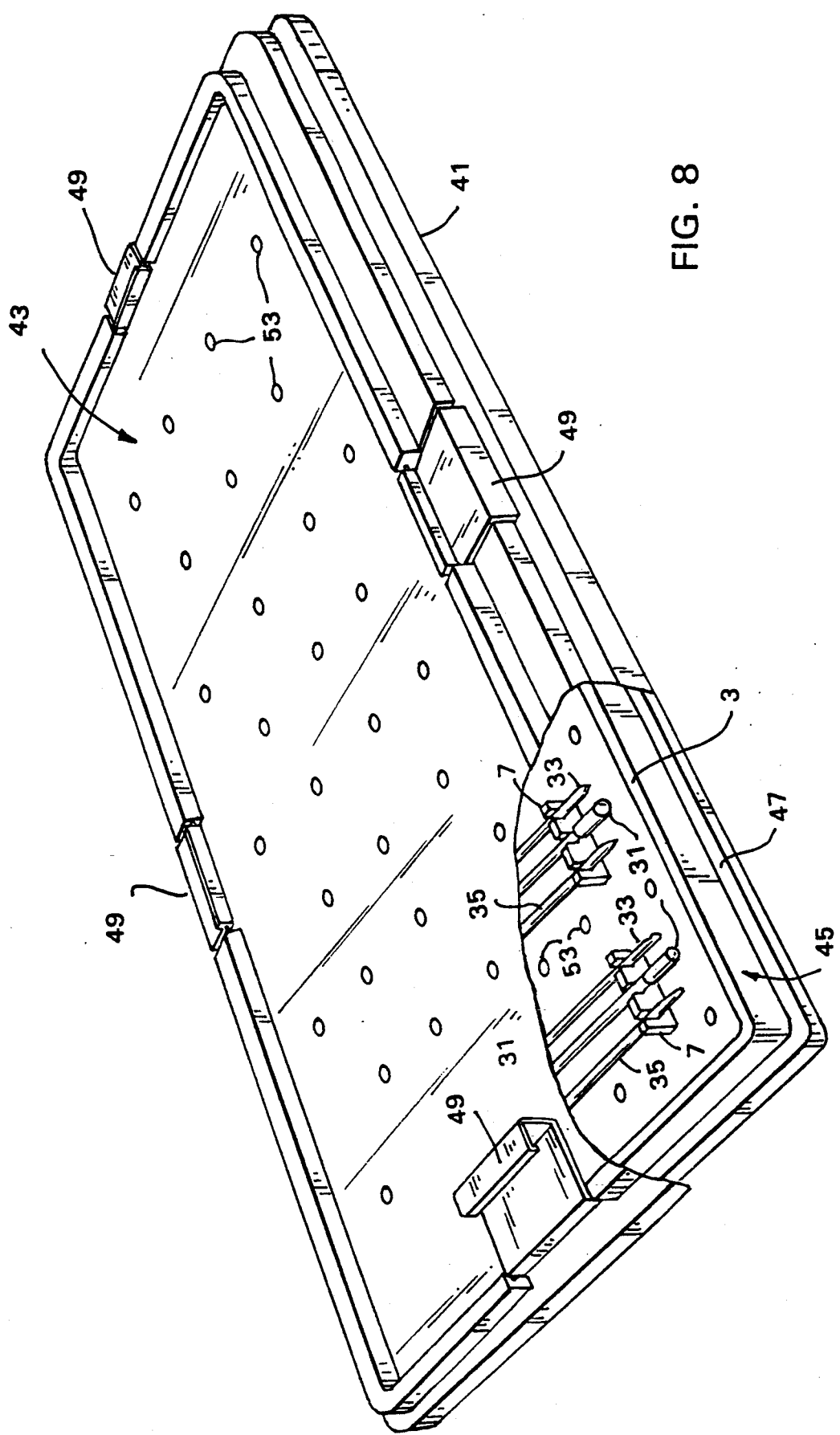
FIG. 8 is a cut-away perspective view of the container and lid showing the finger mat, storage space, insert assembly and instrument sets.

In the preferred embodiment of the invention, insert assembly 1 (FIG. 1) is provided in the form of a tray which fits inside a container 41 which is closed with a lid 43 (FIGS. 7 and 8) for storage or steam autoclaving. Cutouts 44 facilitate lifting insert 1 out of container 41. Insert 1, container 41 and lid 43 are preferably made of a high temperature plastic, such as Ultem (a registered trademark of General Electric Co.) or Radel (a registered trademark of Amoco Petroleum Products). Mounting surface 3 of the tray is spaced from the base of the container, thereby providing a storage space 45 for additional surgical instruments. A silicon finger mat 47 is preferably disposed in the base of container 41 below mounting surface 3 of insert 1, finger mat 47 providing a cushion for additional instruments contained in storage space 45.

Lid 43 is removably secured to container 41 by stainless steel spring latches 49. Spring latches 49 are held pivotally to lid 43 by hinge pins 51, shown in outline in FIG. 7. Ventilation holes 53 are provided in the container, lid and inserts to afford even distribution of heat during the steam sterilization process.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An apparatus, comprising:
   a container;
   a plurality of differently-sized, reusable arthroscopic shaver instruments having a limited useful life, the shaver instruments being color-coded by size;
   a plurality of sets of notched standoffs of different sizes for receiving a corresponding plurality of the differently-sized arthroscopic shaver instruments, the notched standoffs being color-coded in correspondence with the shaver instruments received therein;
   a lid for the container; and
   a plurality of counters for recording the number of times the arthroscopic shaver instruments are used, the plurality of counters corresponding to the plurality of sets of different sized notched standoffs, the counters being color-coded in correspondence with the arthroscopic shaver instruments received in the notched standoffs corresponding thereto.

2. The apparatus of claim 1, wherein the notched standoffs for receiving the arthroscopic shaver instruments and the plurality of counters are mounted on a removable tray adapted to fit within the container.

3. The apparatus of claim 2, wherein the removable tray includes a mounting surface which is spaced from a base of the container, thereby providing a space for storing additional instruments.

4. The apparatus of claim 3, further comprising a silicon finger mat disposed on the base of the container, the finger mat providing a cushion for the additional instruments.

5. The apparatus of claim 1, wherein the container, the arthroscopic shaver instruments, the means for receiving the arthroscopic shaver blades, the lid and the plurality of counters are autoclavable.

* * * * *